United States Patent [19]

McFarlane

[11] Patent Number: 5,573,521
[45] Date of Patent: Nov. 12, 1996

[54] REINFORCED CHOLANGIOGRAM CATHETER

[76] Inventor: Richard H. McFarlane, 2571 Kaneville Rd., Geneva, Ill. 60134

[21] Appl. No.: 390,110

[22] Filed: Feb. 17, 1995

Related U.S. Application Data

[63] Continuation of Ser. No. 712,033, Jun. 7, 1991, abandoned.

[51] Int. Cl.⁶ .................................................. A61M 25/00
[52] U.S. Cl. ............................................ 604/282; 604/280
[58] Field of Search .................................. 604/270, 280, 604/282, 95; 606/157; 128/656–658, 772

[56] References Cited

U.S. PATENT DOCUMENTS

| | | |
|---|---|---|
| 3,780,740 | 12/1973 | Rhea . |
| 4,516,970 | 5/1985 | Kaufman et al. ................... 604/270 |
| 4,769,014 | 9/1988 | Russo ................................ 604/270 |
| 5,017,193 | 5/1991 | Fields ............................... 604/270 |

Primary Examiner—Corrine M. McDermott
Attorney, Agent, or Firm—Malloy & Malloy, P.A.

[57] ABSTRACT

A Reinforced Cholangiogram Catheter including a flexible main length and a distal section. The distal section comprises an elongate flexible tube section and an enlarged head member integrally formed with the tube section and also defines a shoulder therebetween. The tube section has a substantially uniform exterior and interior diameter. The enlarged head member is integrally formed with the tube section and has a generally larger exterior diameter than the tube section. A substantially rigid elongate support tube is disposed within the distal section extending generally from the head member a predetermined distance within the tube section. The support tube is uncollapsible and is structured and dimensioned to reinforce the tube section to prevent it from being compressed along any part thereof. In the preferred embodiment, the enlarged head member has a generally truncated conical shape and includes a section of widest diameter with exterior surfaces that are selectively rounded to form a shoulder of the catheter. The shoulder of the catheter is sized and configured to stoppingly abut a sealing member fastened around a portion of a duct in which the support tube is positioned.

13 Claims, 1 Drawing Sheet

REINFORCED CHOLANGIOGRAM CATHETER

This application is a continuation of application Ser. No. 07/712,033 filed Jun. 7, 1991, now abandoned.

BACKGROUND OF THE INVENTION

1. Field of the Invention

This invention relates generally to catheters and in particular to cholangiogram catheters which are retained within hollow anatomical structures such as cystic ducts by the fastening of a sealing or clamping member around the duct that exerts a substantial compressive force upon the catheter.

2. Description of the Related Art

Cholangiography generally involves the insertion of a catheter into an anatomical duct such as the cystic duct followed by the introduction of a radio-opaque or other contrast medium into the ductal system, for the purpose of radiographic or endoscopic examination of a targeted body organ such as the gallbladder. During the course of cholangiography, a primary concern is that the catheter not slip from the position in which it has been placed in the duct, which may occur by reason of a back pressure against the catheter that can be built up from the forcing of the contrast medium forwardly into the duct. Another major concern is the avoidance of leakage of contrast medium backwards through the duct past the catheter head.

In the past, various techniques of retaining the catheter in place within the cystic duct and sealing fluid flow around the catheter have included simple ligature, Javid clamp, and a loosely applied hemoclip. In addition, cholangiogram catheters have included heads with abruptly-defined flash shoulders thereon to aid in forming a seal against leakage. A more recently developed technique has been to tightly fasten an endoscopic surgical clip around an outer wall section of the cystic duct behind the shoulder of the catheter, which clip compresses the outer wall section of the duct and causes the inner wall of the duct to snugly grip the catheter in the zone behind its shoulder, thereby inhibiting slippage of the catheter from its position within the duct and preventing leakage of contrast medium backwards past the head of the catheter. Such surgical clips are usually bent or otherwise fastened around the duct by means of a substantial clamping force exerted by a special endoscopic clip-applying instrument.

Because of the size and structure of this type of clip-applying instrument, as well as the relatively confined location in which it is used, it is often very difficult and highly user-dependent to be able to apply just enough clamping pressure on the clip to fasten it sufficiently tight so as to assure retention of the catheter within the duct and to provide an adequate seal between the duct and catheter, but without collapsing or occluding the catheter. As a result, there exists a serious problem of inadvertent occlusion or collapse of the catheter within the duct produced by an overtightening of the clip. Such occlusion or collapse of the catheter can impair or defeat its use and effectiveness for performing the cholangiography and any subsequent endoscopic procedure. Accordingly, there is a recognized need in the art for a cholangiogram catheter which is resistant to deformation produced by an excessive clamping force when a sealing member is tightly fastened around the duct. The present invention is directed toward preventing inadvertent occlusion or collapse of the catheter by providing a headed catheter with a substantially inflexible internal support tube that defines an uncollapsible section of the catheter which cannot easily bend or be compressed along any part of such section.

SUMMARY OF THE INVENTION

The present invention is directed toward a reinforced cholangiogram catheter having an uncollapsible section that resists deformation from a substantial compressive or clamping force applied thereon by a sealing or clamping member which secures the catheter in place within a hollow anatomical duct. The catheter includes a flexible main length and distal section. The distal section comprises an elongate tube section, an enlarged head member integrally formed with the tube section and defining a shoulder therebetween, and substantially inflexible tubular support means disposed within the distal section and defining an uncollapsible section thereof. The elongate tube section is imperforate and has a generally uniform external and internal diameter, the latter defining an internal through flow path. The head member includes a section of widest diameter and a tip zone of narrower diameter having a single aperture therein, and is structured to converge from the widest diameter section to the tip zone. The tubular support means extends generally from the head member a predetermined distance within the distal section. The tubular support means is specifically structured and dimensioned to reinforce the uncollapsible section such that it cannot easily bend or be compressed along any part thereof. In addition, the shoulder of the catheter is sized and configured to stoppingly abut the sealing member so as to prevent the distal section from sliding outwardly from the duct and slipping through the sealing member.

It is an object of the present invention to provide a catheter with an uncollapsible section that is resistant to deformation produced by the substantial clamping force of a sealing member which secures the catheter in place within an anatomical duct.

It is another object of the present invention is to provide a catheter with a tubular support means fixedly disposed within a distal section of the catheter so as to define an uncollapsible section thereof that is substantially inflexible and unbendable.

Yet another object is to provide a catheter having a reinforced section structured to allow a compressive force of substantially large magnitude to be exerted upon a sealing member fastened around a duct in which the catheter is inserted, so as to ensure retention of the catheter therein and prevent leakage of contrast medium while avoiding inadvertent occlusion or collapse of the catheter caused by the compressive force.

Still another object of the present invention is to provide a headed catheter having a shoulder that is structured and dimensioned to abut a sealing member which secures the catheter in place within a duct so as to prevent sliding of the catheter outwardly through the sealing member.

BRIEF DESCRIPTION OF THE DRAWINGS

For a better understanding of the nature of the present invention, reference should be had to the following detailed description taken in conjunction with the accompanying drawings in which.

DETAILED DESCRIPTION OF THE PREFERRED EMBODIMENT

Figure 1:
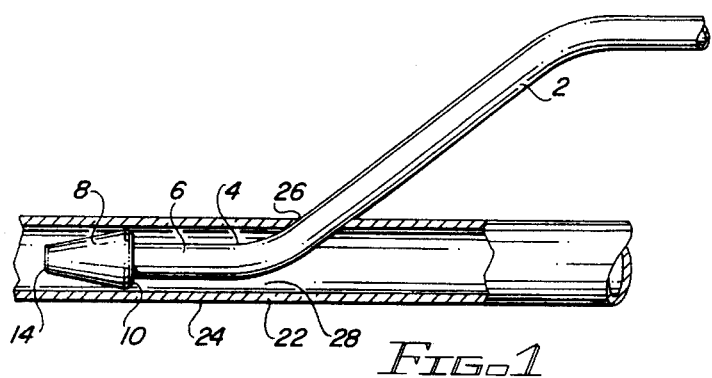
FIG. 1 is a side view of the preferred embodiment of the catheter of the present invention with its distal section positioned within a cystic duct, shown in cut-away.
Figure 3:
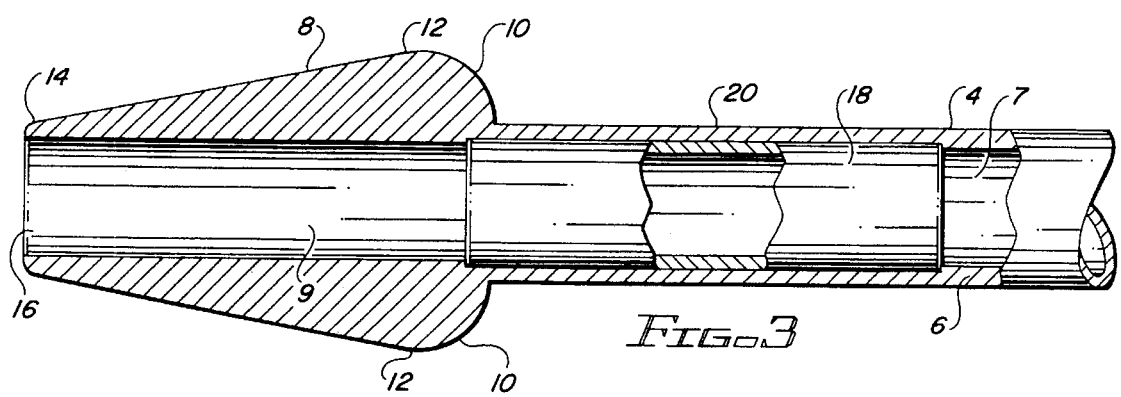
FIG. 3 is a cutaway side view of the preferred embodiment of the catheter of the present invention showing a single elongate support tube disposed within the distal section of the catheter and extending into the head member of the catheter.

Referring to FIG. 1 of the drawings, there is shown the reinforced catheter of the present invention comprising a main length 2 and a distal section 4. The catheter is constructed of a generally flexible plastic material and is preferably formed of polypropylene. Distal section 4 includes an elongate imperforate tube section 6 and a head member 8 integrally formed with tube section 6. As shown in FIG. 3, tube section 6 preferably is of substantially uniform interior and exterior diameter and includes an axial flow channel 7. Head member 8 is of generally larger exterior diameter than the exterior diameter of tube section 6, and includes an axial through path 9 in communication with axial through path 7.

At the juncture of head member 8 and tube section 6 there is formed a shoulder 10. In the preferred embodiment illustrated in the drawings, shoulder 10 will have edges that are selectively rounded so as to prevent the type of injury to the linings of anatomical ducts and organs that may occur when a catheter with an abrupt seal-inducing flash shoulder is removed from the duct. However, those skilled in the art will understand that the catheter of the present invention may include any shoulder that is suitably configured for stoppingly abutting the sealing member which is used to secure distal section 4 in place within a duct, as described below, so as to prevent distal section 4 from sliding outwardly of the duct through the sealing member. Head member 8 preferably has a truncated conical shape and is selectively rounded around the exterior surfaces of a section of widest diameter 12 so as to facilitate intubation of distal section 4 within a cystic duct. Head member 8 is structured to converge from widest diameter section 12 to a narrower tip zone 14 having an aperture 16 in communication with flow channel 7.

The cholangiogram catheter of the present invention also includes a tubular support means disposed within distal section 4 and defining an uncollapsible section 20 thereof. In the preferred embodiment shown in FIG. 3, the tubular support means comprises a single elongate support tube 18 of predetermined length fixedly disposed within tube section 6 by a tight press fit and extending just within head member 8. However, support tube 18 may be positioned within tube section 6 a select proximity from head member 8 to permit bending of distal section 4 just beyond both ends of uncollapsible section 20. Support tube 18 will preferably have a length in the range of 15–17 millimeters, although it will be appreciated by those of ordinary skill in the art that the length of support tube 18 may be selectively increased or decreased from this preferred range. In the preferred embodiment, support tube 18 is constructed of stainless steel. It will be understood, however, that support tube 18 may be constructed of any suitable material, preferably one that is lightweight and noncorrosive, and including other metallic materials such as a titanium alloy. If support tube 18 is formed of a metallic material, a non-metallic coating may be provided on the surfaces of support tube 18 to further prevent conditions for contamination and corrosion.

Support tube 18 is substantially inflexible and unbendable, and reinforces uncollapsible section 20 so that it cannot easily bend or be compressed along any part thereof. In particular, support tube 18 is specifically structured and dimensioned to withstand deformation caused by substantial compressive forces which are exerted against it when a sealing or clamping member is fastened tightenly around the duct into which distal section 4 has been inserted, as more fully described below. Such clamping or compressive forces are of much greater magnitude than the pressures generally exerted upon a catheter by the ductal tissues defining the incision through which the catheter is introduced into the anatomical duct or by the walls of the anatomical duct into which the catheter has been inserted. Support tube 18 therefore enables uncollapsible section 20 to resist deformation, occlusion or collapse that might inadvertently occur on an unreinforced catheter by reason of the substantial compressive forces that are applied when a sealing or clamping member is fastened tightly around the duct in surrounding relation to the intubated catheter.

Figure 2:
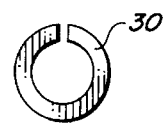
FIG. 2 is a front elevation view of a conventional Sutiate Titanium Clip seen in FIGS. 4 and 5 that is fastened around the duct with special clip-applying instruments.
Figure 4:
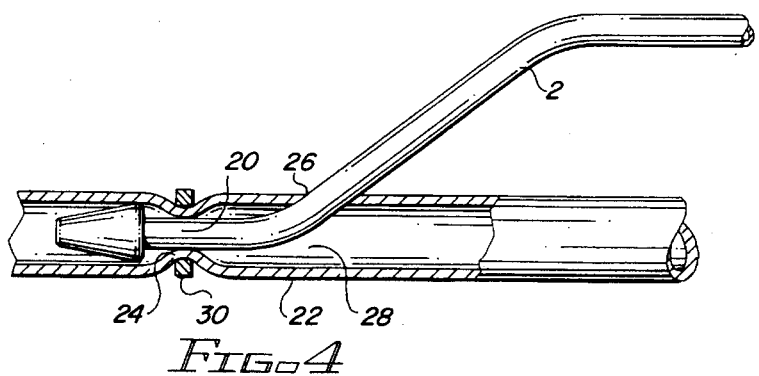
FIG. 4 is a side view of the catheter as depicted in FIG. 1 but with its distal section secured within the cystic duct, shown in cutaway, by a surgical clip fastened around the sealing section of the duct and the uncollapsible section of the catheter.

In the use of the catheter of the present invention, distal section 4 is positioned within an anatomical duct 22 with uncollapsible section 20 disposed adjacent a targeted sealing section 24 of duct 22, as shown in FIG. 1. In order to insert distal section 4 into an anatomical duct 22 such as a cystic duct that lacks a natural outside entrance, an incision 26 is made in duct 22 and main length 2 of the catheter is bent as necessary to allow distal section 4 to be at a different attitudinal angle than main length 2 upon insertion. Following intubation of distal section 4, a sealing or clamping member is bent or fastened around sealing section 24 of duct 22 sufficiently tight so as to assure retention of distal section 4 within duct 22 and to prevent leakage of contrast medium backwardly past sealing section 24 towards section 28 of duct 22. When tightly fastened as aforesaid, the sealing member compresses the outer wall of sealing section 24 and causes its inner wall to firmly bear down upon and snugly grip uncollapsible section 20, as shown in FIG. 4. One widely used type of sealing member used for this purpose is the metal surgical clip 30 known as a Sutiate Titanium Clip, shown separately in FIG. 2. Clip 30 is fastened around sealing section 24 by means of a special clip-applying instrument having jaws which apply a substantial clamping force that bends clip 30 tightly around sealing section 24.

Figure 5:
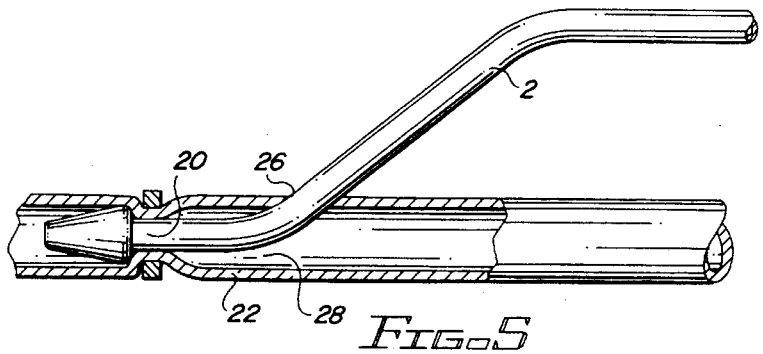
FIG. 5 is a side view of the catheter as depicted in FIG. 4, but with the shoulder of the catheter positioned in stopping abutment with the surgical clip.

Those skilled in the art will appreciate that the present invention enables a substantially greater clamping force to be applied to tightly fasten clip 30 around sealing section 24, while avoiding occlusion or collapse of uncollapsible section 20 of distal section 4, than could be applied in the case of an unreinforced cholangiogram catheter. This substantially greater applied clamping force and consequent tighter fastening of clip 30 produces an increased compression of sealing section 24 around uncollapsible section 20, providing the important advantages of maximizing retention of distal section 4 within duct 22 and virtually eliminating leakage and extravasation. Moreover, if a back pressure is exerted against distal section 4 during the cholangiography as the result of the forcing of contrast medium into duct 22, such that distal section 4 begins to slip outwardly from sealing section 24, shoulder 10 serves the important purpose of preventing distal section 4 from sliding through clip 30. As distal section 4 begins to slip outwardly, shoulder 10 comes into stopping abutment with clip 30 and halts any further outward slippage of distal section 4, as shown in FIG. 5. If the user desires to avoid the possibility of slippage of distal section 4 during the cholangiography, then after clip 30 has been fastened around sealing section 24, main length 2 may be pulled outwardly until shoulder 10 abuts clip 30.

Although the present invention has particular application to cholangiogram catheters that are inserted within a cystic duct, it will be understood that the present invention may be embodied in any type of tubular surgical instrument that is secured by a sealing or clamping member within a hollow linear organ structure, so as to prevent the inadvertent collapse or occlusion of that tubular surgical instrument when a substantial compressive force is applied to fasten the sealing member. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A reinforced catheter having a main length and a distal section, said distal section comprising:
   (a) an elongate, flexible tube section having a substantially uniform exterior and interior diameter;
   (b) a head member integrally formed with said tube section, said head member being of a generally larger exterior diameter than said tube section and forming a shoulder therebetween; and
   (c) substantially rigid tubular support means disposed within said distal section, said tubular support means extending generally from said head member a predetermined distance within said tube section, said tubular support means defining an uncollapsible section of said tube section, said tubular support means being structured and dimensioned to reinforce said uncollapsible section such that said uncollapsible section cannot be compressed along any part thereof.

2. A reinforced catheter as recited in claim 1 wherein said tubular support means is fixedly positioned within said distal section.

3. A reinforced catheter as recited in claim 2 wherein said tubular support means includes at least a portion extending within said head member.

4. A reinforced catheter as recited in claim 2 wherein said tubular support means is disposed a predetermined distance from said head member.

5. A reinforced catheter as recited in claim 1 wherein said tubular support means comprises a single elongate support tube of predetermined length.

6. A reinforced catheter as recited in claim 5 wherein said support tube has a length of at least 8 millimeters.

7. A reinforced catheter as recited in claim 5 wherein said support tube is constructed of a metallic material.

8. A reinforced catheter as recited in claim 7 wherein said support tube is constructed of stainless steel.

9. A reinforced catheter as recited in claim 7 further comprising a non-metallic coating on interior and exterior surfaces of said support tube.

10. A reinforced catheter as recited in claim 1 wherein said shoulder is configured and dimensioned to stoppingly abut a sealing member fastened around a portion of a duct in which said uncollapsible section is positioned.

11. A reinforced catheter as recited in claim 1 wherein said shoulder includes edges that are selectively rounded.

12. A reinforced catheter as recited in claim 1 wherein said head member has a generally truncated conical shape and includes a section of widest diameter with exterior surfaces that are selectively rounded.

13. A reinforced catheter having a main length and a distal section, said distal section comprising:
   (a) an elongate, flexible tube section having a substantially uniform exterior and interior diameter;
   (b) a head member integrally formed with said tube section, said head member being of a generally larger exterior diameter than said tube section and forming a shoulder therebetween;
   (c) substantially inflexible tubular support means disposed within said distal section, said tubular support means extending generally from said head member a predetermined distance within said tube section, said tubular support means defining an uncollapsible section of said tube section, said tubular support means being structured and dimensioned to reinforce said uncollapsible section such that said uncollapsible section cannot easily bend or be compressed along any part thereof; and
   (d) said tubular support member comprising a single elongate support tube of predetermined length constructed of a titanium alloy.

* * * * *